US 6,723,080 B1

(54) PREPACKAGED DIAPER CHANGING KIT

(76) Inventors: Peter D. Habib, 1202 Sewickley Heights Dr., Sewickley, PA (US) 15143; Caroline Y. Habib, 1202 Sewickley Heights Dr., Sewickley, PA (US) 15143

( * ) Notice: Subject to any disclaimer, the term of this patent is extended or adjusted under 35 U.S.C. 154(b) by 0 days.

(21) Appl. No.: 09/399,471

(22) Filed: Sep. 21, 1999

(51) Int. Cl.$^7$ .............................................. A61F 13/20
(52) U.S. Cl. ................................ 604/385.06; 206/570
(58) Field of Search .................. 604/385.06, 385.01; 206/777, 438, 812, 216, 210, 510; 248/118; 2/102

(56) References Cited

U.S. PATENT DOCUMENTS

| | | | |
|---|---|---|---|
| 3,970,217 A | * 7/1976 | Culbertson et al. ........... 221/80 |
| 4,221,221 A | * 9/1980 | Ehrlich ........................ 128/284 |
| 4,702,378 A | * 10/1987 | Finkel et al. ................. 206/581 |
| 4,964,859 A | * 10/1990 | Feldman ................... 604/385.1 |
| 5,071,414 A | * 12/1991 | Elliott ....................... 604/385.1 |
| 5,255,817 A | 10/1993 | Reiland et al. |
| D341,027 S | * 11/1993 | Godden et al. ................ D3/74 |
| 5,409,105 A | * 4/1995 | Appelbaum et al. ......... 206/6.1 |
| 5,443,161 A | * 8/1995 | Jonese ........................ 206/581 |
| 5,569,230 A | * 10/1996 | Fisher et al. .............. 604/385.1 |
| 5,575,784 A | * 11/1996 | Ames-Ooten et al. ... 604/385.1 |
| 5,582,605 A | * 12/1996 | Lepie ........................ 604/385.1 |
| 5,707,031 A | * 1/1998 | Creighton-Young ........ 248/118 |
| 5,875,490 A | * 3/1999 | Woodard et al. ............... 2/49.1 |
| 6,004,307 A | * 12/1999 | Colon et al. ............. 604/385.1 |
| 6,105,170 A | * 8/2000 | Lisciandro et al. ............ 2/102 |
| 6,168,022 B1 | * 1/2001 | Ward et al. .................. 206/581 |

* cited by examiner

*Primary Examiner*—Weilun Lo
*Assistant Examiner*—Michele Kidwell
(74) *Attorney, Agent, or Firm*—Carl A. Ronald

(57) ABSTRACT

A prepackaged diaper changing kit which is compact and convenient to carry and use and which is capable of being both dispensed from a conventional vending machine, as well as being displayed on shelves and sold in conventional retail establishments. A preferred embodiment of this prepackaged diaper changing kit includes a disposable diaper, at least one (1), and more preferably two (2), prepackaged moist baby wipes, a prefolded baby liner, a prepackaged instant hand sanitizer and a prefolded disposable plastic bag. These items are preferably prepackaged together in a durable waterproof outer wrapper, such as an opaque plastic outer wrap film. The prepackaged diaper changing kit in accordance with the present invention provides all of the supplies needed to change a diaper for, for example, a newborn or infant, and, when finished, allows the user to secure and discard the dirty or wet diaper, as well as the used moist baby wipes and other left over packaging materials, in a safe and convenient manner.

7 Claims, 6 Drawing Sheets

PREPACKAGED DIAPER CHANGING KIT

BACKGROUND AND SUMMARY OF THE INVENTION

The present invention relates generally to new and novel improvements in a prepackaged diaper changing kit. More particularly, the present invention relates to a prepackaged diaper changing kit which is compact and convenient to carry and use and which is capable of being both dispensed from conventional vending machines, as well as being displayed on shelves and sold in conventional retail establishments.

Having the necessary items to change a newborn or infant's diaper, particularly when away from the home, is a recurring challenge for parents and others caring for newborns and infants. A diaper bag is often carried which includes supplies, such as a number of diapers, baby wipes, blankets and/or towels, as well as other items used in changing a newborn or infant's diaper. Such diaper bags are often bulky and cumbersome and are particularly inconvenient to transport and store in crowded public facilities, such as, for example, shopping centers, airports, sport stadiums and arenas, amusement parts, museums and restaurants. Furthermore, when using such diaper bags, often one or more of the supplies are used up or missing and this complicates the task of changing the newborn or infant's diaper. In addition, many people have the need to change a newborn or infant's diaper only occasionally, such as when grandchildren visit their grandparents, or when newborns or infants visit other relatives and/or friends who do not have young children themselves. In such situations, diapers and other supplies must either be carried with the newborn or infant or the host must purchase diapers and other supplies, generally available only in relatively large quantities, for the visiting newborn or infant.

In addition to being convenient and easy to use, the prepackaged diaper changing kit in accordance with the present invention provides several sanitation and environmental advantages. In particular, the prepackaged diaper changing kit in accordance with the current invention minimizes the transfer of bacteria and germs from the caregiver to the newborn or infant, minimizes the transfer of bacteria and germs from the newborn or infant to the environment, minimizes the transfer of bacteria and germs from newborn or infant to newborn or infant on the changing table, is readily disposable in an environmentally friendly manner and provides all of the necessary supplies to carry out the diaper changing process.

Accordingly, an object of the present invention is the provision of a prepackaged diaper changing kit which includes a disposable diaper, as well as the other supplies needed to change a diaper, and which is compact and convenient to carry and use.

Another object of the present invention is the provision of a prepackaged diaper changing kit which includes a disposable diaper, as well as the other supplies needed to change a diaper, and which is capable of being both dispensed from conventional vending machines, as well as being displayed on shelves and sold at conventional retail establishments.

These and other objects of the present invention are attained by a prepackaged diaper changing kit which is compact and convenient to carry and use and which is capable of being both dispensed from conventional vending machines, as well as being displayed on shelves and sold in conventional retail establishments. A preferred embodiment of this prepackaged diaper changing kit includes a disposable diaper, one (1), or more preferably two (2), prepackaged moist baby wipes, a prefolded baby liner, a prepackaged instant hand sanitizer and a prefolded disposable plastic bag. These items are prepackaged together in a durable waterproof outer wrapper, such as an opaque plastic outer wrap film. The prepackaged diaper changing kit in accordance with the present invention provides all of the supplies needed to change a diaper for, for example, a newborn or infant, and, when finished, allows the user to secure and discard the dirty or wet diaper, as well as used moist baby wipes and other packaging materials, in a safe and convenient manner.

Other advantages and novel features of the present invention will become apparent in the following detailed description of the invention when considered in conjunction with the accompanying drawings.

DETAILED DESCRIPTION OF THE DRAWINGS

Figure 1:
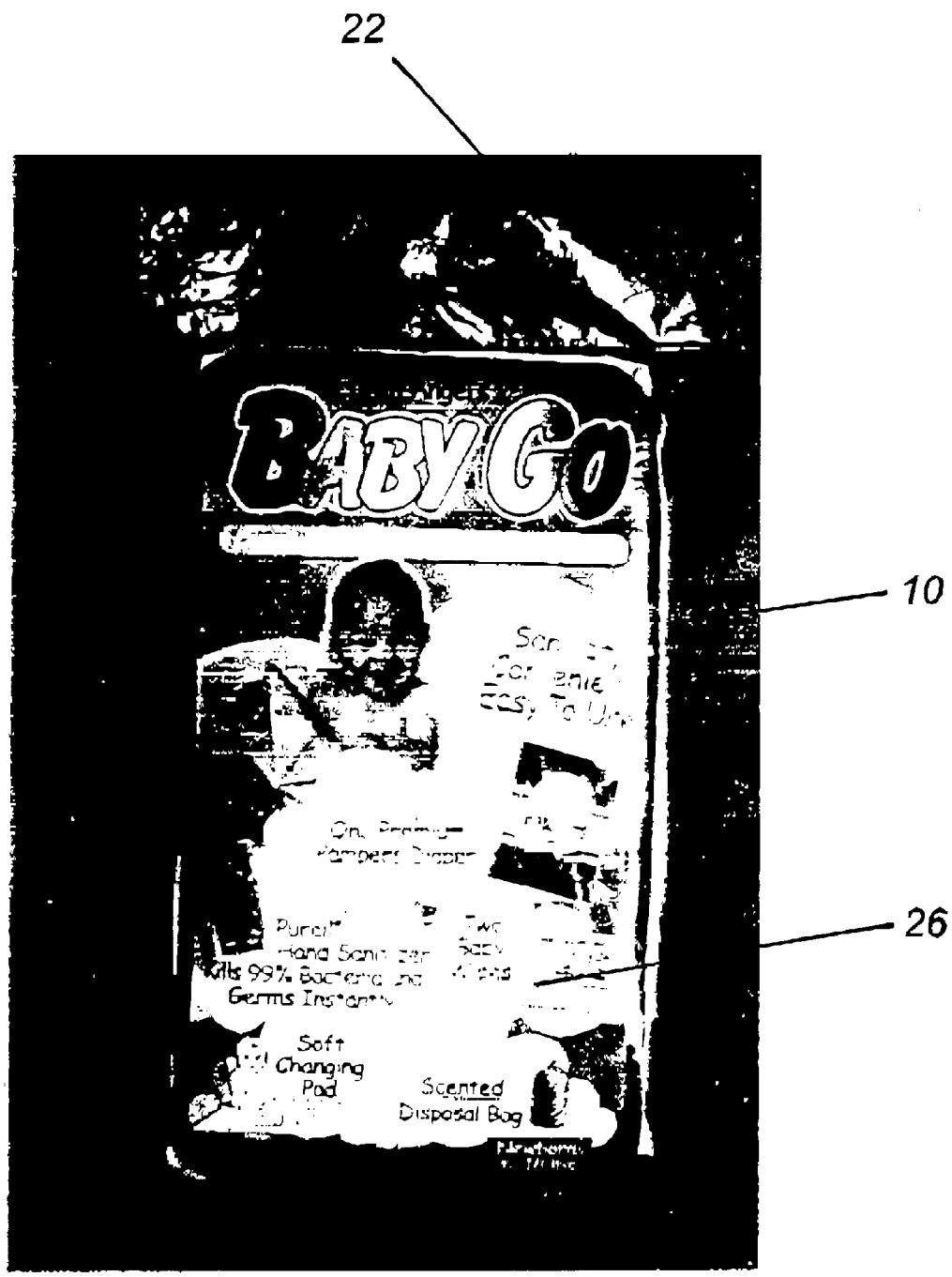
FIG. 1 is a photograph showing a top view of a prepackaged diaper changing kit in accordance with a preferred embodiment of the present invention.
Figure 2:
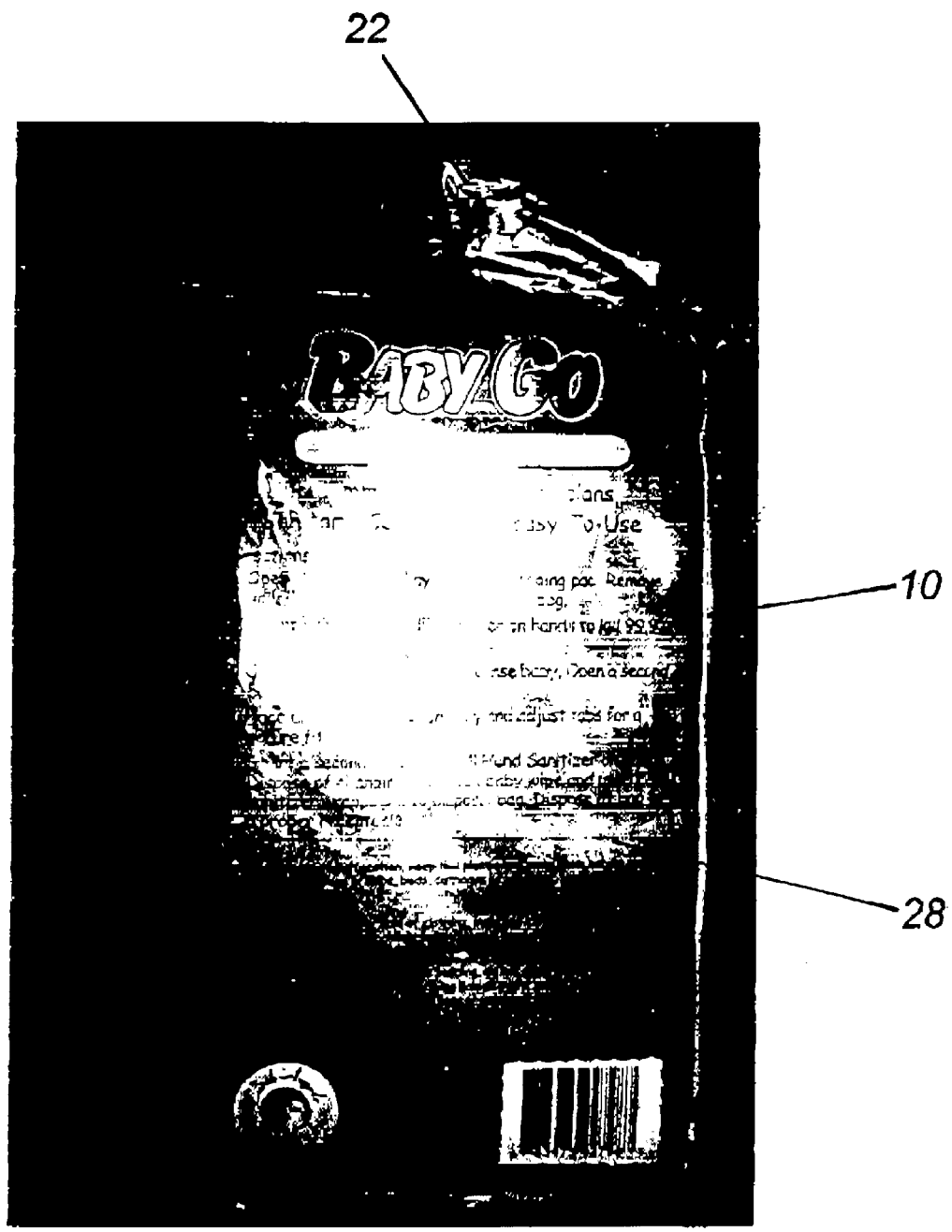
FIG. 2 is a photograph showing a bottom view of the prepackaged diaper changing kit in accordance with the preferred embodiment of the present invention shown in FIG. 1.
Figure 3:
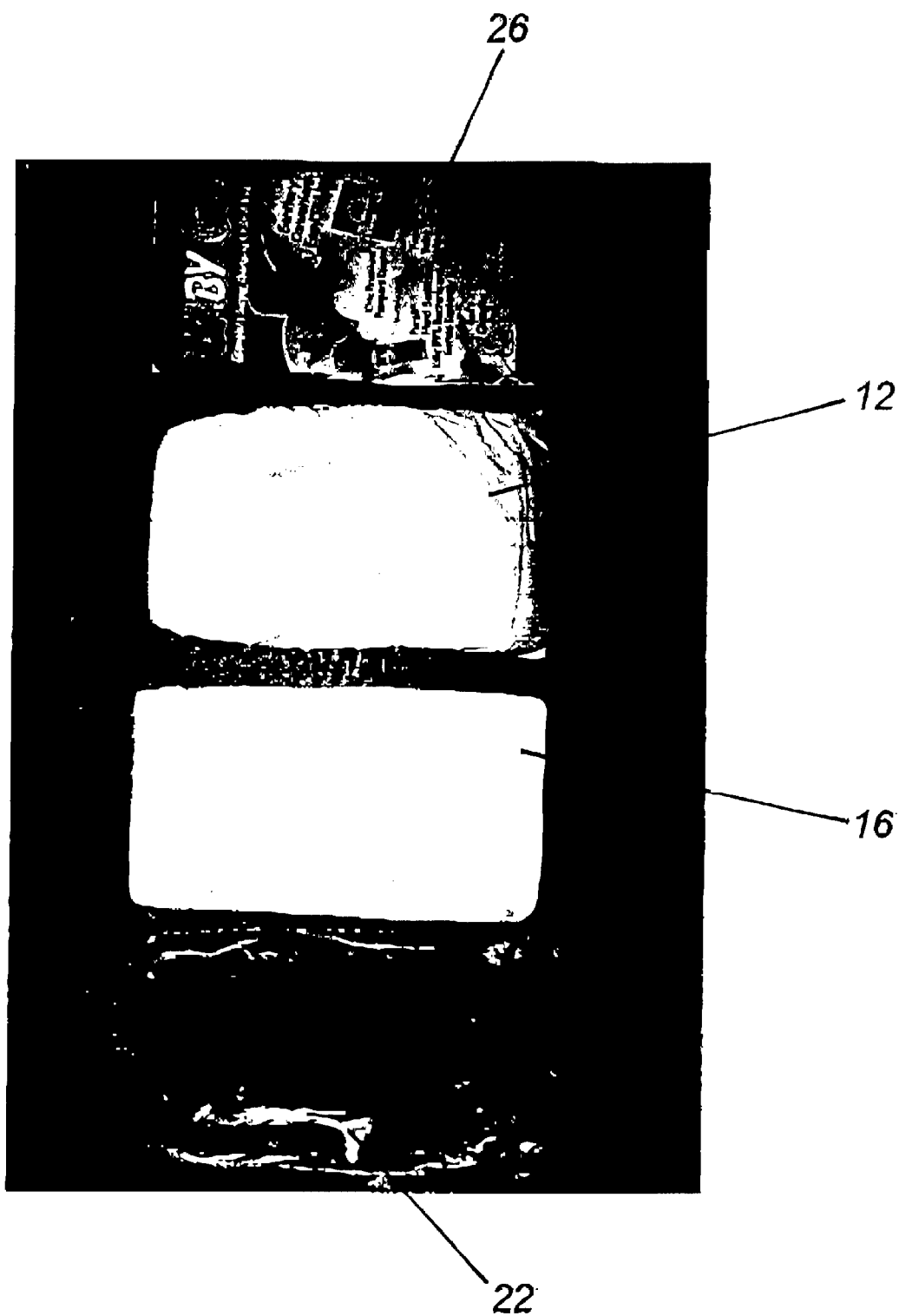
FIG. 3 is a photograph showing a top view of the prepackaged diaper changing kit in accordance with the preferred embodiment of the present invention shown in FIG. 1, with the exterior packaging opened and the contents of the prepackaged diaper changing kit removed therefrom.
Figure 4:
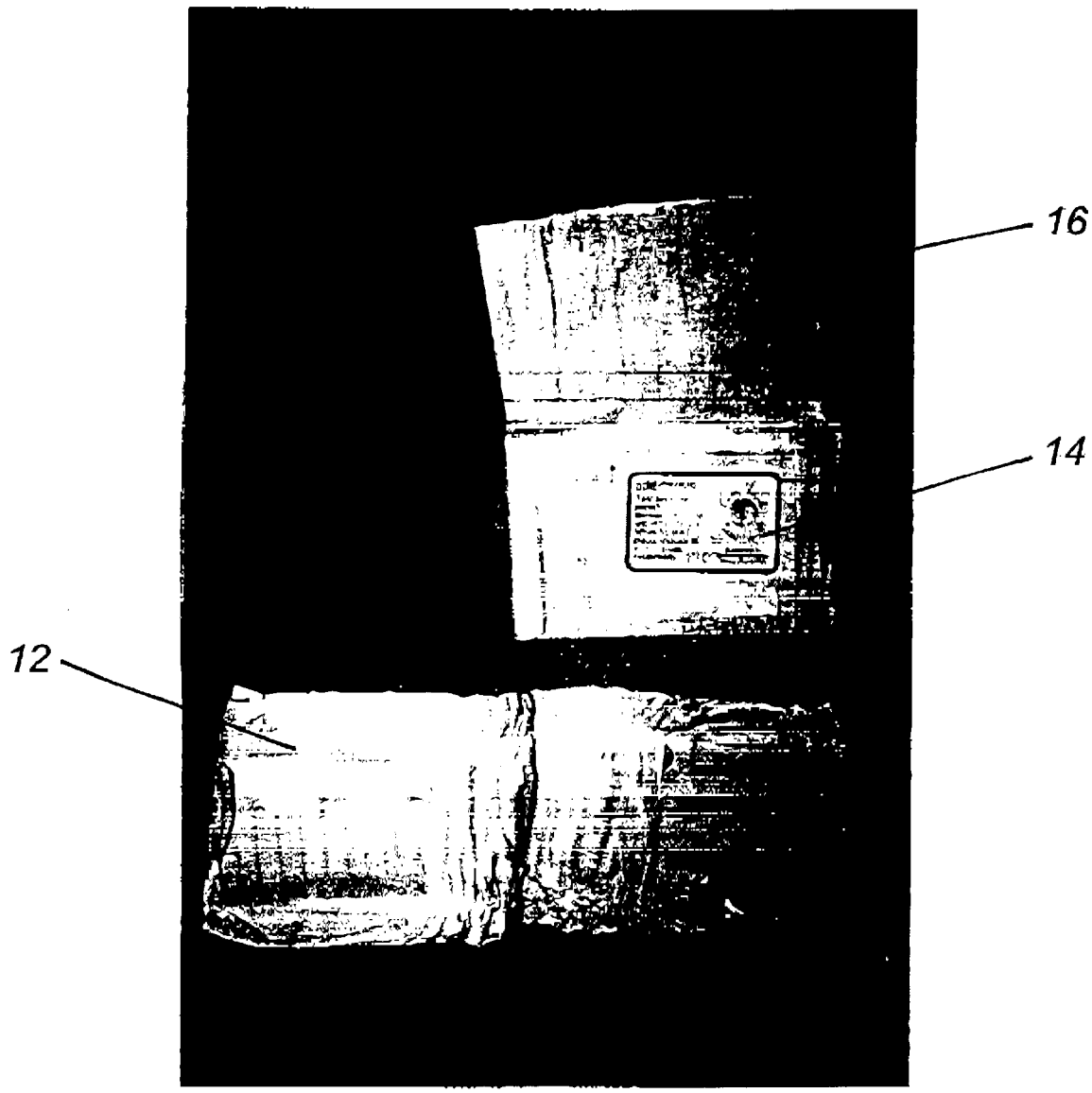
FIG. 4 is a photograph showing a top view of the contents of the prepackaged diaper changing kit in accordance with the preferred embodiment of the present invention shown in FIG. 1, with the contents of the prepackaged diaper changing kit partially unfolded and opened.
Figure 5:
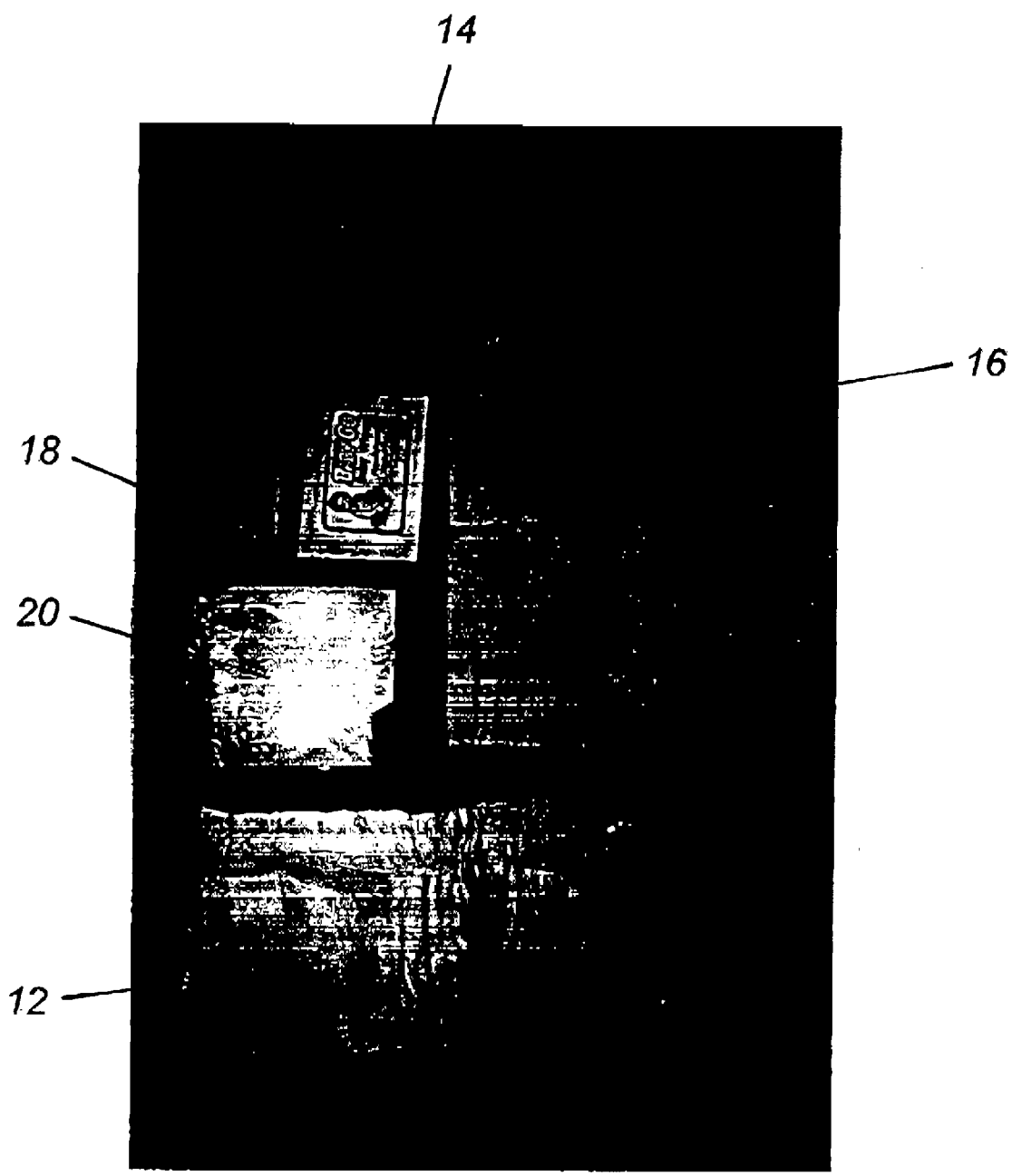
FIG. 5 is a photograph showing a top view of the contents of the prepackaged diaper changing kit in accordance with the preferred embodiment of the present invention shown in FIG. 1, with the contents of the prepackaged diaper changing kit further unfolded and opened.
Figure 6:
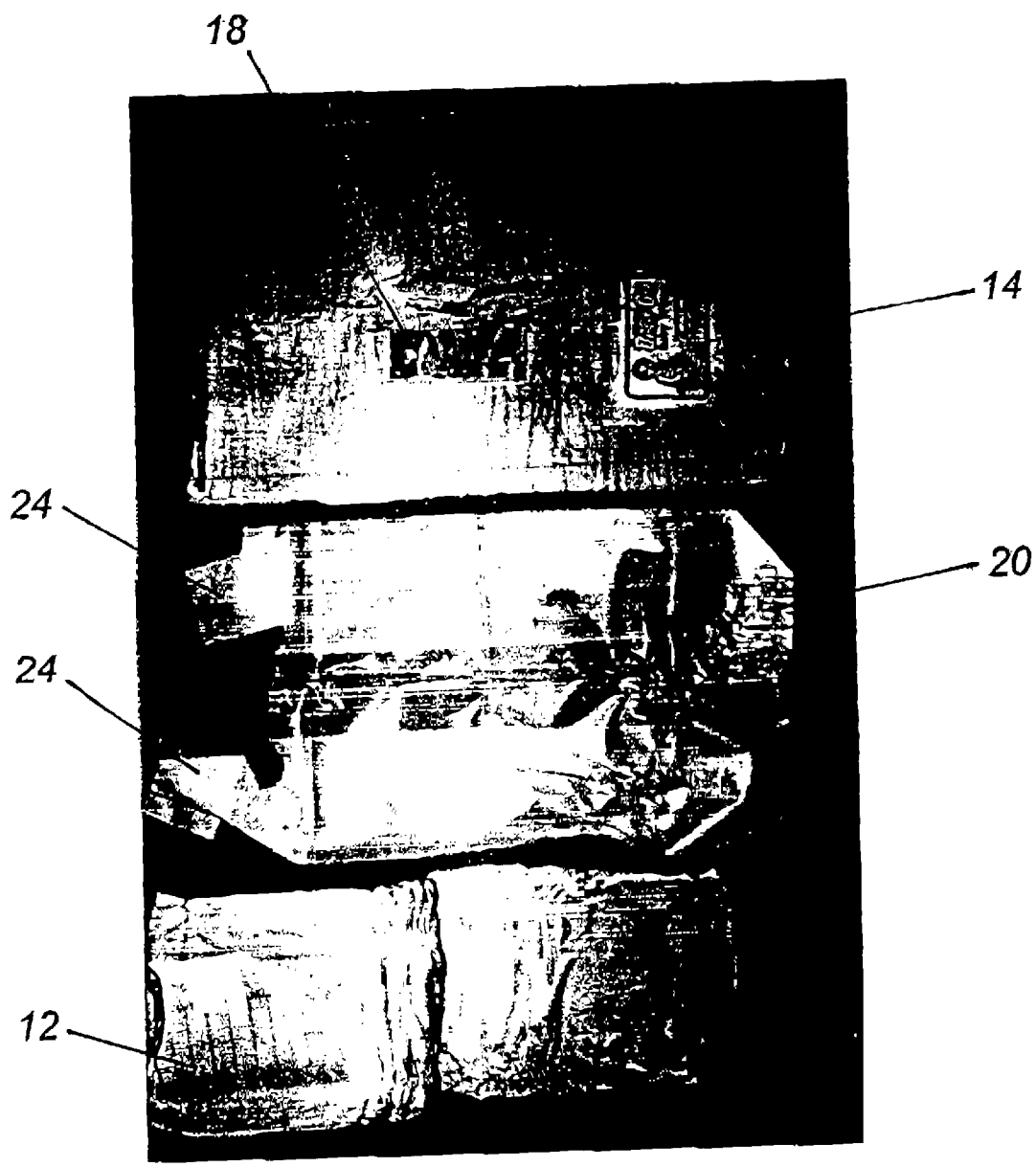
FIG. 6 is a photograph showing a top view of the contents of the prepackaged diaper changing kit in accordance with the preferred embodiment of the present invention shown in FIG. 1, with the contents of the prepackaged diaper changing kit further unfolded and opened.

In the following detailed description of a preferred embodiment of the present invention, reference is made to the accompanying drawings which, in conjunction with this detailed description, illustrate and describe a preferred embodiment of a prepackaged diaper changing kit in accordance with the present invention. Referring to FIGS. 1 through 6, which illustrate a top view of a prepackaged diaper changing kit in accordance with a preferred embodiment of the present invention, a bottom view of the prepackaged diaper changing kit in accordance with the preferred embodiment of the present invention shown in FIG. 1, a top view of the prepackaged diaper changing kit in accordance with the preferred embodiment of the present invention shown in FIG. 1, with the exterior packaging opened and the contents of the prepackaged diaper changing kit removed therefrom, a top view of the contents of the prepackaged diaper changing kit in accordance with the preferred embodiment of the present invention shown in FIG. 1, with the contents of the prepackaged diaper changing kit partially unfolded and opened, a top view of the contents of prepackaged diaper changing kit in accordance with the preferred embodiment of the present invention shown in FIG. 1, with the contents of the prepackaged diaper changing kit further unfolded and opened, and a top view of the contents of the prepackaged diaper changing kit in accordance with the preferred embodiment of the present invention shown in FIG. 1, with the contents of the prepackaged diaper changing kit further unfolded and opened, respectively, prepackaged diaper changing kit, generally identified by reference number 10, is compact and convenient to carry and use and is capable of being both dispensed from conventional vending machines, as well as being displayed on shelves and sold in conventional retail establishments.

Prepackaged diaper changing kit 10 generally includes disposable diaper 12, prepackaged moist baby wipes 14, baby liner 16, prepackaged instant hand sanitizer 18 and disposable plastic bag 20, all of which are prepackaged in exterior packaging 22. Disposable diaper 12 is preferably a "snug-fit baby diaper" of conventional design and can be of different sizes for newborns, infants, toddlers, and even older children and adults, of different sizes. In a preferred embodiment of prepackaged diaper changing kit 10, two (2) different sizes of disposable diaper 12 are anticipated, a smaller size being suitable for newborns and infants of up to approximately eighteen (18) pounds and a larger size suitable for infants and toddlers from approximately eighteen (18) pounds up to approximately thirty six (36) pounds. Other sizes for disposable diaper 12 could also be used, for example, one size for newborns and infants of up to approximately twelve (12) pounds, a larger size suitable for infants from approximately twelve (12) pounds to approximately twenty four (24) pounds and yet a larger size suitable for infants and toddlers from approximately twenty four (24) pounds up to approximately thirty six (36) pounds. Still larger sizes for disposable diaper 12 could be used in prepackaged diaper changing kit 10 in accordance with the present invention, if desired, for still larger children and/or adults.

At least one (1), and more preferably two (2), prepackaged moist baby wipes 14 are included in each prepackaged diaper changing kit 10. Prepackaged moist baby wipes 14 preferably have a rectangular configuration in the range of four (4) to eight (8) inches in height and in the range of six (6) to twelve (12) inches in width and most preferably are approximately seven (7) inches in height by approximately eight (8) inches in width and are folded to fit into an outer wrapper, preferably at least partially fabricated from a waterproof barrier material such as, for example, a foil or plastic material. The outer wrapper preferably provides a barrier to maintain the moisture level of the moist baby wipe packaged inside, but should also be relatively easy for the user to open to remove the moist baby wipe. The moist baby wipes are preferably fabricated from an air-laid porous material which is saturated with a hypoallergenic mildly fragrant cleansing lotion and are, most preferably, alcohol free.

Baby liner 16 consists of a prefolded rectangular piece, preferably in the range of eleven (11) to fifteen (15) inches in height and in the range of fifteen (15) to twenty four (24) inches in width and most preferably is approximately thirteen and one half (13½) inches in height and approximately eighteen (18) inches in width. Baby liner 16 is preferably fabricated from a soft absorbent clothlike material on which to place the newborn or infant, such as a 4-ply scrim material. Baby liner 16 can be used, if needed, to clean the newborn or infant and can also be used to wrap up the wet or dirty diaper and other items to be discarded therein.

Prepackaged instant hand sanitizer 18 is preferably prepackaged in a relatively flat waterproof packaging. Most preferably, prepackaged instant hand sanitizer consists of a prefolded sanitizing hand towel saturated with a sanitizing solution including a moisturizer, vitamins A and E and aloe therein. The prefolded sanitizing hand towel is approximately five (5) inches in height by approximately seven and one half (7½) in width when unfolded. A suitable prepackaged prefolded sanitizing hand towel is distributed by GOJO Industries, Inc. in Akron, Ohio. Alternatively, prepackaged instant hand sanitizer 18 could consist of a prepackaged portion of a hand sanitizing solution, such as prepackaged portion of PURELL® hand sanitizer having 0.043 fluid ounces (1.33 ml) distributed by GOJO Industries, Inc. in Akron, Ohio. Prepackaged instant hand sanitizer 18 preferably contains no water, requires no towels and kills 99.9% of bacteria and germs.

Disposable plastic bag 20 is preferably fabricated as a "junior" trash bag from a scented plastic material and includes outwardly extending arms 24 which allow a dirty or wet diaper, as well as used moist baby wipe(s) and other packaging material, to be placed inside disposable plastic bag 20 and outwardly extending arms 24 are then tied together to secure the dirty or wet diaper, as well as the used moist baby wipe(s) and other packaging material, inside of disposable plastic bag 20. Disposable plastic bag 20 and its contents can then be discarded when convenient in any suitable trash receptacle. Disposable plastic bag 20 is preferably prefolded to fit inside of exterior packaging 22.

Exterior packaging 22 is preferably dimensioned to be slightly larger than the assembly consisting of disposable diaper 12, one (1), or more preferably two (2), prepackaged moist baby wipes 14, baby liner 16, prepackaged instant hand sanitizer 18 and disposable plastic bag 20 so disposable diaper 12, one (1), or more preferably two (2), prepackaged moist hand wipes 14, baby liner 16, prepackaged instant hand sanitizer 18 and disposable plastic bag 20 fit snugly inside of exterior packaging 22. Exterior packaging 22 is preferably fabricated from an opaque plastic wrap film material, most preferably white, although a transparent, or a translucent material, such as a transparent plastic wrap film material, could alternatively be used to allow the contents inside exterior packaging 22 to be viewed when prepackaged diaper changing kit 10 is displayed.

However, exterior packaging 22 is most preferably fabricated from an opaque material having information such as the contents of prepackaged diaper changing kit 10, directions as to its use and disposal, warning and/or cautions about the use and/or disposal of prepackaged diaper changing kit 10, the manufacturer's name and address and other marketing and factual information, as desired, preprinted thereon. Such information is preferably preprinted on both the front and the back of exterior packaging 22. Alternatively, such information could be preprinted on only one of the front and back of exterior packaging 22, or, if desired, on neither the front or back of exterior packaging 22. In addition, exterior packaging 22 is preferably substantially waterproof to protect the contents of exterior packaging 22 from moisture, as well as from dirt and other environmental debris.

Most preferably, exterior packaging 22 is fabricated from an opaque plastic wrap film material having a top portion presealed approximately one (1) inch from the top of exterior packaging 22 and an aperture substantially centered in this presealed top portion to allow prepackaged diaper changing kit 10 to be displayed on a projecting rod type display. When exterior packaging 22 having a presealed top portion is used, the contents of prepackaged diaper kit 10 are inserted through an opening present in the bottom of exterior packaging 22 and the bottom portion of exterior packaging 22 is then sealed using, for example, a heat plastic "welding" process and/or an adhesive.

If exterior packaging 22 is fabricated from a transparent or a translucent material, a front graphics card and/or a rear graphics card can be placed in front of and/or in back of, respectively, disposable diaper 12 to show through exterior packaging 22. The front graphic card and/or the rear graphics card can include information about the contents of prepackaged diaper changing kit 10, directions as to its use and disposal, warnings and/or cautions about the use and/or disposal of prepackaged diaper changing kit 10, the manufacturer's name and address and other marketing and factual information, as desired.

Other items could also be included in prepackaged diaper changing kit 10, if desired, such as, for example, prepackaged baby powder, prepackaged diaper rash ointment, prepackaged teething reliever ointment and/or a disposable bib. Prepackaged diaper changing kit 10 is capable of being readily dispensed from conventional vending machines. Such vending machines may be located in facilities such as, for example, airports, shopping centers, gas stations, highway rest areas, family restaurants, sports facilities and arenas, amusement parts and children recreation centers. In addition, individual prepackaged diaper changing kits 10 can be displayed on a shelf and sold in various retail establishments, such as, for example, convenience stores, grocery stores, pharmacies and department stores. In addition, multiple prepackaged diaper changing kits 10 can be prepackaged and distributed together in, for example, "six (6) packs" which could, for example, be given as a "maternity" gift to new parents by hospitals, be given as baby shower gifts or sold in multiple quantity packages in various retail establishments, such as, for example, convenience stores, grocery stores, pharmacies and department stores. It would be clear to those having ordinary skill in the relevant art that other quantities of multiple prepackaged diaper changing kits 10 could also be sold, such as, for example "twelve (12) packs" and/or "twenty four (24) packs," if desired. Prepackaged diaper changing kits 10 could also be marketed and sold by mail order or over the Internet.

To form prepackaged diaper changing kit 10, disposable plastic bag 20 is folded and is placed along with one (1), or more a preferably two (2), prepackaged moist baby wipes 14 and prepackaged instant hand sanitizer 18 inside folded baby liner 16. Folded baby liner 16 is then placed inside folded disposable diaper 12. If desired, one or both of a front graphics card and/or a rear graphics card are then placed in front of and/or behind, respectively, folded disposable diaper 12 and this assembly is then placed in exterior packaging 22 through a bottom opening in exterior packaging 22. The bottom opening of exterior packaging 22 is then sealed using, for example, a heat plastic "welding" process and/or an adhesive.

To use prepackaged diaper changing kit 10, exterior packaging 22 is opened and folded disposable diaper 12 is opened to facilitate the removal of baby liner 16. Baby liner 16 is then unfolded and placed on the surface where the newborn or infant is to be changed. The newborn or infant is placed on baby liner 16 and the dirty or wet diaper is removed and placed into disposable plastic bag 20. Prepackaged instant hand sanitizer 18 is then opened and applied on the hands of the person who is changing the diaper of the newborn or infant to kill 99.9% of bacteria and germs. One (1), or if needed two (2), prepackaged moist baby wipes 14 are then opened and the newborn or infant is wiped and cleaned. If needed, baby liner 16 can also be used to wipe and clean the newborn or infant. Disposable diaper 12 is then placed on the newborn or infant and the tabs are adjusted as desired to provide a secure fit on the newborn or infant. Items to be discarded, including used moist baby wipe(s), opened prepackaged moist baby wipe wrapper(s), exterior packaging 22 and, if present, one (1) or both of the front graphics card and/or the rear graphics card are then rolled into baby liner 16 and baby liner 16 and its enclosed contents are placed in disposable plastic bag 20 for disposal. Prepackaged instant hand sanitizer 18 is then again applied on the hands of the person who changed the diaper of the newborn or infant to again kill 99.9% of bacteria and germs and prepackaged instant hand sanitizer 18 is also placed within disposable plastic bag 20. Outwardly extending arms 24 of disposable plastic bag 20 are then tied together and disposable plastic bag 20, along with its contents, can be carried and discarded, when convenient, into a suitable trash receptacle. Since disposable plastic bag 20 is preferably fabricated from a scented plastic material, little or no odor is left behind.

Accordingly, although the present invention has been described above in detail, the same is by way of illustration and example only and is not to be taken as a limitation on the present invention. It is apparent to those having a level of ordinary skill in the relevant art that other variations and modifications in the prepackaged diaper changing kit in accordance with the present invention, as described and shown herein, could be readily made using the teachings of the present invention. For example, other arrangement for inserting and sealing the contents of prepackaged diaper kit 10 could readily be utilized. Accordingly, the scope and content of the present invention are to be defined only by the terms of the appended claims.

What is claimed is:

1. A prepackaged diaper changing kit comprising:

a disposable diaper folded inwardly along a longitudinal centerline;

one or more baby changing supply items selected from the group consisting of a prepackaged moist baby wipe, a prepackaged instant hand sanitizer, a prepackaged baby powder, a prepackaged diaper rash ointment, a baby changing liner, and a disposable plastic bag, wherein said one or more baby changing supplies are placed inside said disposable diaper;

exterior packaging which encloses said disposable diaper; and a prepackaged teething reliever ointment positioned inside said disposable diaper.

2. A prepackaged diaper changing kit comprising:

a disposable diaper folded inwardly along a longitudinal centerline;

one or more baby changing supply items selected from the group consisting of prepackaged moist baby wipes, a prepackaged instant hand sanitizer, a prepackaged baby powder, a prepackaged diaper rash ointment, wherein said one or more baby changing supply items are placed inside said disposable diaper;

a baby changing liner;

a disposable plastic bag;

exterior packaging which encloses said disposable diaper, said baby changing liner and said disposable plastic bag; and a disposable bib.

3. The prepackaged diaper changing kit in accordance with claim 2, wherein said exterior packaging includes text and/or images preprinted on a front surface thereof.

4. The prepackaged diaper changing kit in accordance with claim 2, wherein said exterior packaging in includes text and/or images preprinted on a rear surface thereof.

5. The prepackaged diaper changing kit in accordance with claim 2, wherein said exterior packaging is substantially opaque.

6. The prepackaged diaper changing kit in accordance with claim 2 wherein said prepackaged diaper changing kit is capable of being dispensed from a conventional vending machine.

7. A prepackaged diaper changing kit comprising:

a disposable diaper folded inwardly along a longitudinal centerline;

one or more baby changing supply items selected from the group consisting of prepackaged moist baby wipes, a prepackaged instant hand sanitizer, a prepackaged baby powder, and a prepackaged diaper rash ointment, wherein said one or more baby changing supplies are placed in side said disposable diaper;

a baby changing liner;

a disposable plastic bag;

exterior packaging which encloses said disposable diaper, said baby changing liner and said disposable plastic bag; and a prepackaged teething reliever ointment positioned inside said disposable diaper.

* * * * *